US00PP37592P2

(12) United States Plant Patent
Byrne et al.

(10) Patent No.: US PP37,592 P2
(45) Date of Patent: Aug. 18, 2026

(54) PEACH TREE NAMED 'TX2B449LW'

(50) Latin Name: *Prunus persica*
Varietal Denomination: TX2B449LW

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 19/336,370

(22) Filed: Sep. 22, 2025

(51) Int. Cl.
*A01H 5/08* (2018.01)

(52) U.S. Cl.
USPC ..... Plt./195

(58) Field of Classification Search
USPC ..... Plt./156, 180, 194, 195
See application file for complete search history.

(56) References Cited

U.S. PATENT DOCUMENTS

PP28,077 P3 6/2017 Byrne et al.

OTHER PUBLICATIONS

U.S. Appl. No. 19/336,141, filed Sep. 22, 2025, Byrne et al.
U.S. Appl. No. 19/336,148, filed Sep. 22, 2025, Byrne et al.
U.S. Appl. No. 19/336,164, filed Sep. 22, 2025, Byrne et al.
U.S. Appl. No. 19/336,169, filed Sep. 22, 2025, Byrne et al.
U.S. Appl. No. 19/336,358, filed Sep. 22, 2025, Byrne et al.
U.S. Appl. No. 19/336,361, filed Sep. 22, 2025, Byrne et al.
U.S. Appl. No. 19/336,363, filed Sep. 22, 2025, Byrne et al.
U.S. Appl. No. 19/336,365, filed Sep. 22, 2025, Byrne et al.
U.S. Appl. No. 19/336,368, filed Sep. 22, 2025, Byrne et al.
U.S. Appl. No. 19/336,372, filed Sep. 22, 2025, Byrne et al.
U.S. Appl. No. 19/336,375, filed Sep. 22, 2025, Byrne et al.
U.S. Appl. No. 19/336,377, filed Sep. 22, 2025, Byrne et al.
U.S. Appl. No. 19/336,380, filed Sep. 22, 2025, Byrne et al.
U.S. Appl. No. 19/336,383, filed Sep. 22, 2025, Byrne et al.
U.S. Appl. No. 19/336,385, filed Sep. 22, 2025, Byrne et al.
Byrne and Anderson, 2013. White Delight peach series: Four medium-chill, subacid, white-fleshed peaches. HortScience 48(8):1056-1058.

*Primary Examiner* — Karen M Redden
(74) *Attorney, Agent, or Firm* — Dentons US LLP

(57) ABSTRACT

Disclosed is a new variety of *Prunus persica* named 'TX2B449LW'. This new variety, which requires approximately 450 chilling units of dormancy, is considered to be a peach tree of early season maturity, which produces white-fleshed, subacid fruit that are very firm, has a 60-80% red to maroon blush over a yellow ground color and suitable fresh market use.

5 Drawing Sheets

Latin name of the genus and species of the plant claimed: *Prunus persica.*

Variety denomination: 'TX2B449LW'.

CROSS-REFERENCE TO RELATED APPLICATIONS

Peach trees developed under the same breeding program as 'TX2B449LW' include the co-pending applications listed below.

| U.S. application Ser. No. | Title |
|---|---|
| U.S. 19/336,141 | PEACH TREE NAMED 'TX3C490LWP' |
| U.S. 19/336,148 | PEACH TREE NAMED 'TRH2E68L' |
| U.S. 19/336,164 | PEACH TREE NAMED 'TRH3B53L' |
| U.S. 19/336,169 | PEACH TREE NAMED 'TRH3C114W' |
| U.S. 19/336,358 | PEACH TREE NAMED 'TRH2E121L' |
| U.S. 19/336,361 | PEACH TREE NAMED 'TRH3A17' |
| U.S. 19/336,363 | PEACH TREE NAMED 'TRH2E120LW' |
| U.S. 19/336,365 | PEACH TREE NAMED 'TRH3C113LW' |
| U.S. 19/336,368 | PEACH TREE NAMED 'TRH3E88LW' |
| U.S. 19/336,372 | PEACH TREE NAMED 'TX2C465CW' |
| U.S. 19/336,385 | PEACH TREE NAMED 'TRH2B102LW' |
| U.S. 19/336,375 | PEACH TREE NAMED 'TRH1C104LW' |
| U.S. 19/336,377 | PEACH TREE NAMED 'TRH3C111' |

-continued

| U.S. application Ser. No. | Title |
|---|---|
| U.S. 19/336,380 | PEACH TREE NAMED 'TRH2C108W' |
| U.S. 19/336,383 | PEACH TREE NAMED 'TRH2E116L' |

BACKGROUND OF THE INVENTION

This invention relates to a peach tree and, more specifically, to a peach tree referred to as a variety of *Prunus persica* named 'TX2B449LW', which requires approximately 450 chilling units of dormancy, produces a firm, clingstone, white-fleshed, subacid peach with a 60-80% red to maroon blush over a yellow ground color that matures early in the season. The present peach tree was the result of an ongoing Stone Fruit Breeding Program in College Station, Brazos County, Texas. To this end, controlled crosses were made each year to produce seedling populations from which improved progenies are evaluated and selected. 'TX2B449LW' was derived from a population created by crossing the high chill, white-fleshed, subacid peach 'White Delight Four' (not patented) with pollen of the low-chill, subacid, white-fleshed, nectarine 'Smooth Delight One' (patented). The seed from the 'White Delight Four' x 'Smooth Delight One' hybrid family were planted in 2010 in an experimental plot in Somerville, TX. 'TX2B449LW' was marked for subsequent observation in 2012 and noted as having exceptional characteristics.

'TX2B449LW' was bud grafted onto virus-free 'Nemaguard' (not patented, The Brooks and Olmo Register of Fruit and Nut Varieties, 3rd Ed., American Society of Horticultural Science Press, Alexandria, VA, 1997) peach at the nursery site in Oakdale, CA. The variety was subsequently planted and evaluated as two-year and older trees in Pleasanton (2018-2019), Somerville (2014-2023) and Fairfield (2014-2020), Texas. This evaluation clearly demonstrated that the re-propagated trees were true to the characteristics of the original seedling in all observable aspects.

SUMMARY OF THE INVENTION

The 'TX2B449LW' peach is characterized by producing clingstone, white-fleshed, subacid fruit that ripens early in the season and produces a firm fruit with a 60-80% red to maroon blush over a yellow ground color. In this regard, the present variety of peach tree bears fruit that are ripe for commercial harvesting and shipment in mid-May, when the fruit is grown in the medium chill zone of Texas. 'TX2B449LW' blooms about one month before its female parent 'White Delight Four' (not patented, US App. Pub. No. 2016/0205831 P1, abandoned), and a few days after its pollen parent 'Smooth Delight One' (patented, U.S. Plant Pat. No. 28,077). It ripens ~ 6 weeks before its female parent and a few days after its pollen parent. 'TX2B449LW' differs from its white-fleshed, subacid, peach female parent as it ripens 6 weeks before and requires 300 less chilling hours to fruit. It differs from its subacid, white-fleshed, nectarine pollen parent as it is a peach. 'TX2B449LW' differs from the medium chill, subacid, white-fleshed commercial peach cultivars 'White Delight One' (not patented, US App. Pub. No. 2016/0205833 P1, abandoned) and 'White Delight Two' (US App. Pub. No. 2016/0205832 P1, abandoned) as it has showy rather than non showy flowers, reniform rather than globose glands, requires 100 less chilling hours to fruit properly and blooms about 10 days before 'White Delight One' and 'White Delight Two'. This new subacid, white-fleshed, clingstone, early-ripening peach exhibits potential to be commercialized in regions that have chilling requirements that are moderately low.

BRIEF DESCRIPTION OF THE DRAWINGS

This new variety of peach tree is illustrated by the accompanying photographs of 3-year old to 5-year old plants grown in Somerville, Texas, as provided in FIGS. 1-5. These photographs show the plant's typical fruit, foliage, and flowers, and the colors shown are as true as can be reasonably obtained by conventional photographic procedures.

DETAILED BOTANICAL DESCRIPTION

Figure 1:
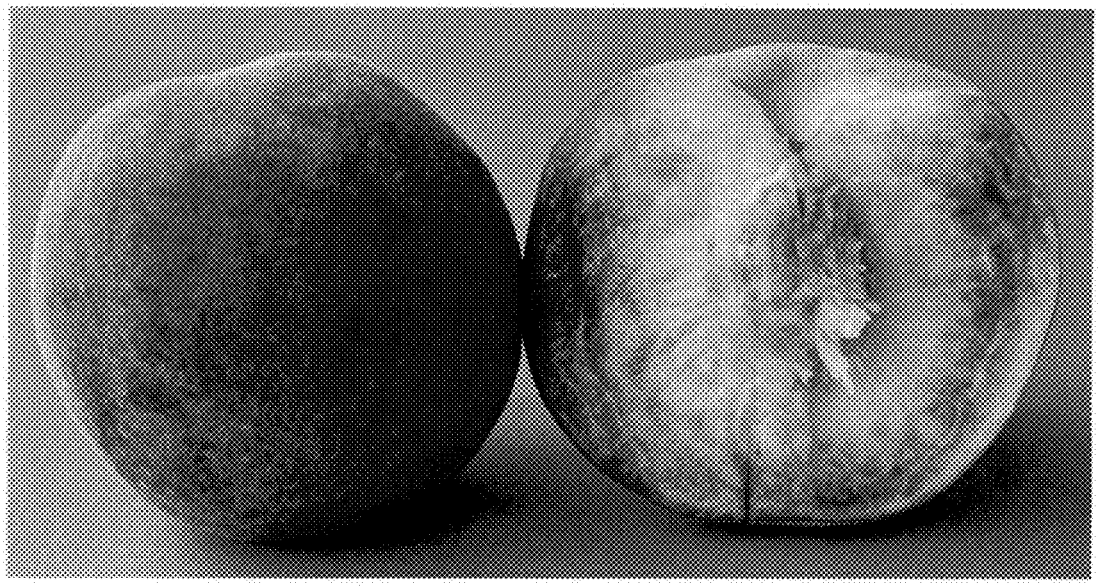
FIG. 1. Fruit of 'TX2B449LW' produced in Somerville, Texas showing external and internal coloration.
Figure 2:
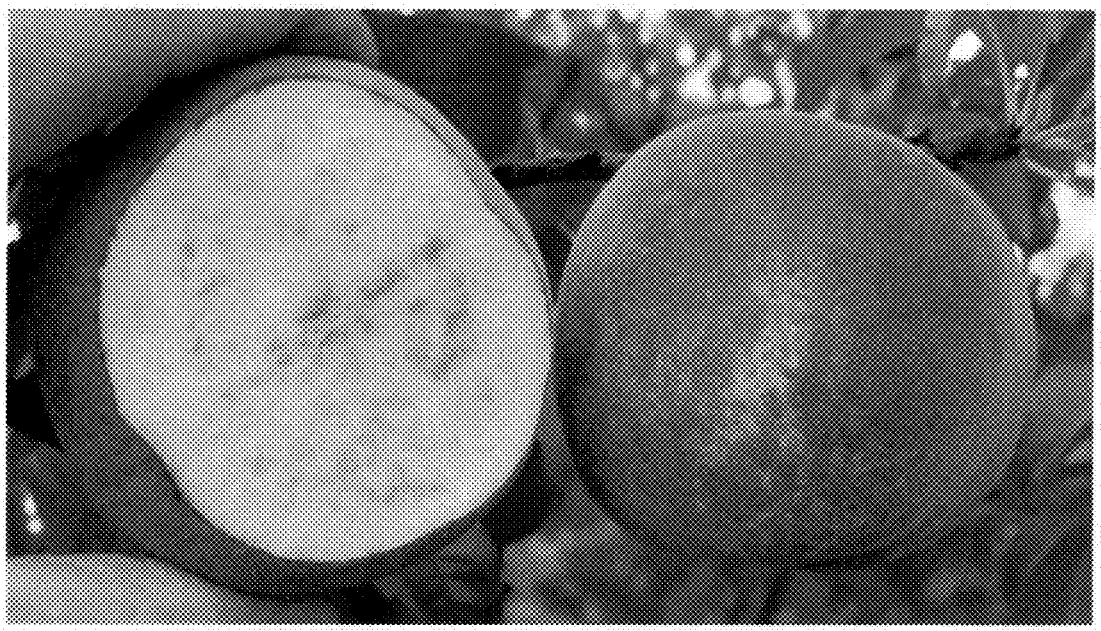
FIG. 2. 'TX2B449LW' fruit produced in Somerville, Texas showing shape and external coloration.
Figure 3:
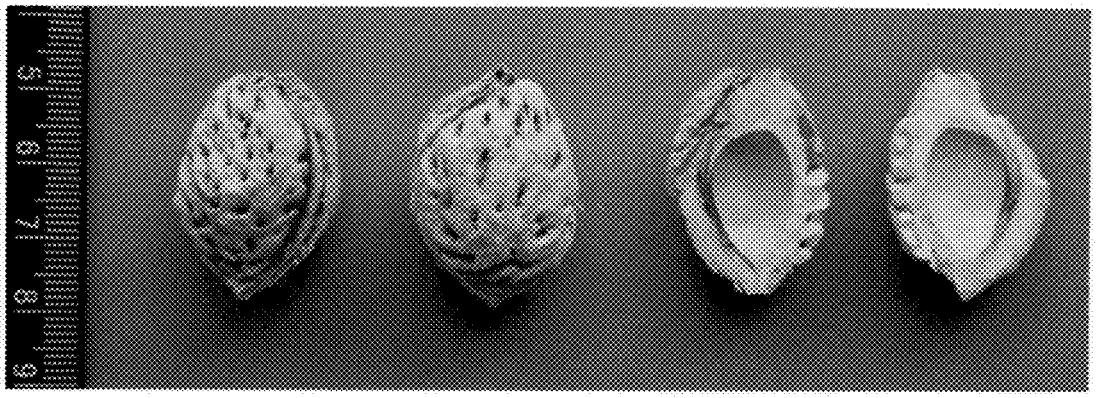
FIG. 3. Photograph of the endocarps of 'TX2B449LW' peach. The ruler is in centimeters.
Figure 4:
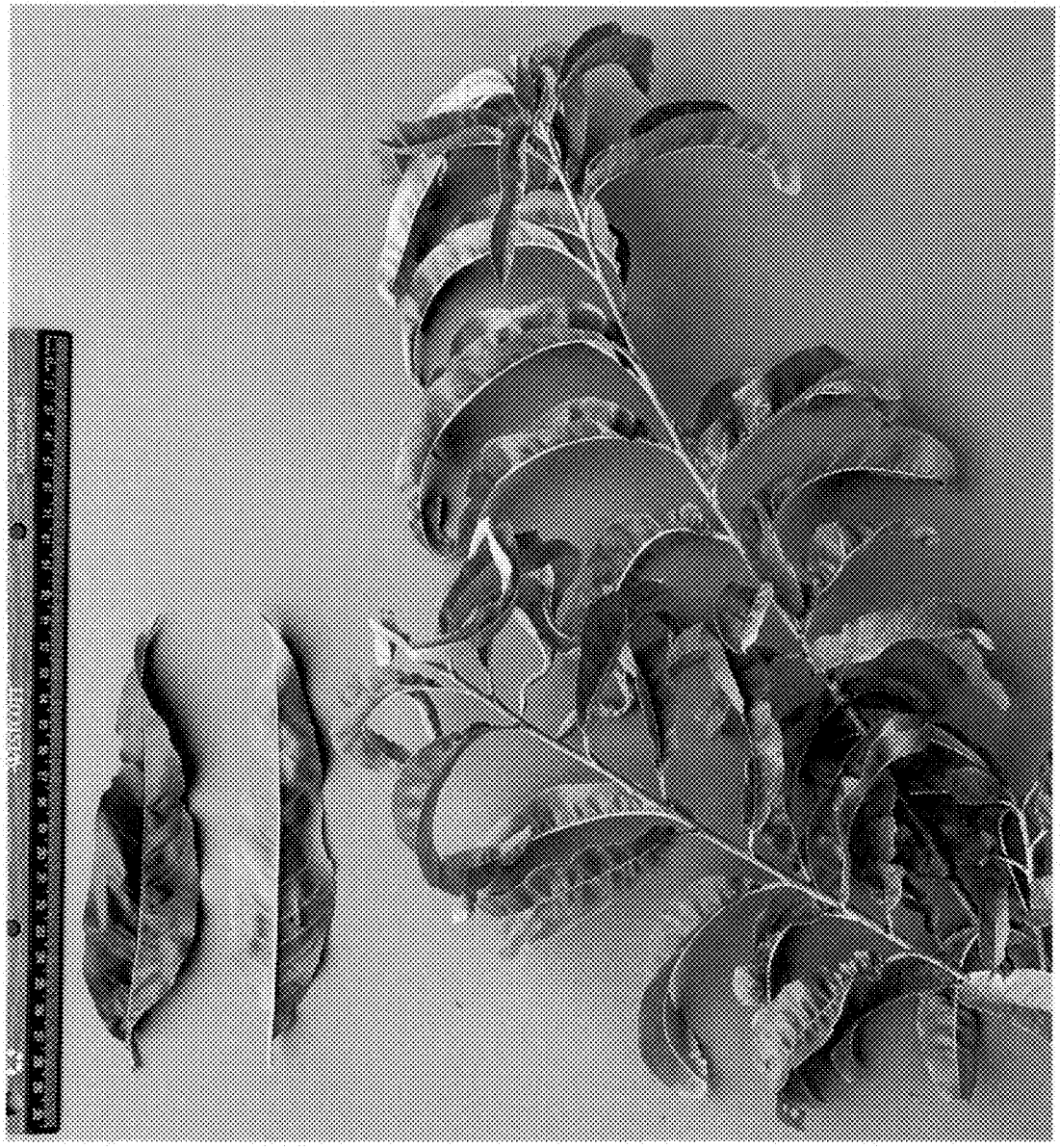
FIG. 4. A stem showing the leaves of 'TX2B449LW' peach. The ruler is in centimeters.
Figure 5:
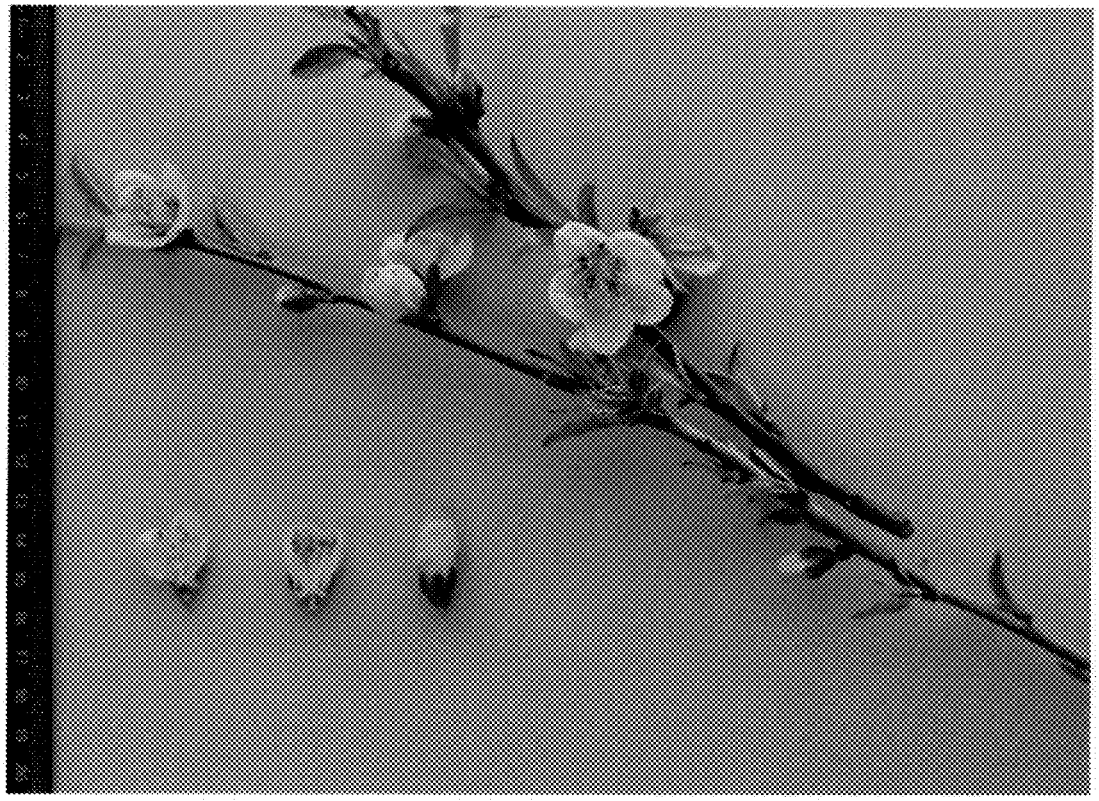
FIG. 5. A stem showing the flowers of 'TX2B449LW' peach. The ruler is in centimeters.

Referring more specifically to the pomological details of this new and distinct variety of peach tree, the following has been observed under the ecological conditions prevailing at the experimental orchards in the medium chill zone of Texas (Fairfield and Somerville). All major color code designations are by reference to The R.H.S. Colour Chart (2001 Edition) provided by The Royal Horticultural Society of Great Britain. Colors are approximate as color depends on horticultural practices such as light level and fertilization rate, among others.

Tree:

*Size*.—Generally average to above average as compared to other common peach cultivars ripening in the early season of maturity.

*Height*.—8 to 9 feet (2.4 to 2.7 m) at the end of the 2024 growing season.

*Width*.—7 feet width (2.1 m) at the end of the 2024 growing season.

*Productivity*.—Produces annually in the medium chill zone of Texas without alternate bearing if temperatures of 28° F. or lower are not experienced during bloom. Trees are self-fertile and must be fruit thinned most years to avoid limb breakage and obtain optimal fruit size. The recommended fruit spacing for early to mid-season ripening fresh market peach cultivars for a full crop is one fruit every 6-8" of one-year old fruiting wood. Trees often set more fruit than needed for a full crop.

*Shape*.—The 'TX2B449LW' peach has been trained an open center configuration but exhibits a semi spreading growth type as seen in peach varieties 'Texprince' (patented, U.S. Plant Pat. No. 14,629) and 'Texking' (patented, U.S. Plant Pat. No. 14,627).

*Current season growth*.—The current season growth for the new variety was approximately 1 to 4 feet (0.3-1.2 m). Vigor is medium to medium high compared to other common peach varieties grown in the medium chill zone of Texas. Regularity of Bearing — Regular in the absence of temperatures of 28° F. or below during bloom and considered hardy in the medium chill zone of Texas.

Trunk:

*Size*.—Approximately 3 inches (7.6 cm) in diameter and 9.5 inches (24.1 cm) in circumference when measured at a distance of approximately 12 inches (30.5 cm) above the soil level, at the end of the 2024 growing season on a three-year old tree.

*Bark texture*.—Considered moderately rough with numerous folds of papery scarf-like skin being present. Bark Coloration — Variable, colors (RHS2001) present are 156B, 156C, and 156D of the Greyed-White Group, 157A of the Green-White Group, 166A, 176A and 176B of the Greyed-Orange Group and 178A and 178B of the Greyed-Red Group.

Branches:

*Size*.—Considered medium to medium large for the species.

*Thickness*.—About 4.4 cm in diameter as measured 10 cm from the trunk on a three-year old tree.

*Surface texture*.—Average and appearing furrowed on wood that is several years old.

*Lenticels*.—Numerous flat, oval lenticels present. The lenticels range in size from approximately 3 to 6 mm in width and were approximately 1 to 1.5 mm in height.

*Current season shoots*.—Surface texture — Substantially glabrous.

*Internode length*.—Approximately 18 to 21 mm as measured in the middle of a current season stem. Color of Mature Branches — The predominant colors (RHS2001) are 156D of the Greyed-White Group, 166A, 166B, 175A and 176A of the Greyed-Orange Group and N200D of the Brown Group.

Leaves:

*Size*.—Considered moderately large for the species. Leaf measurements have been taken from vigorous upright current season growth approximately at mid-shoot.

*Leaf length*.—Approximately 165 to 192 mm.

*Leaf width*.—Approximately 38 to 45 mm.

*Leaf thickness*.—Less than 1 mm.

*Leaf form*.—Lanceolate.

*Leaf tip form*.—Acuminate.

*Leaf upper surface color* (*RHS*2001).—Green varying among 137C and 138A of the Green Group and 146A of the Yellow-Green Group.

*Leaf lower surface color* (*RHS*2001).—Green, 146A and 146B of the Yellow-Green Group.

*Leaf lower mid-vein color* (*RHS*2001).—Light yellow green, 145C, 145D, 150D and 154D of the Yellow-Green Group.

*Leaf margins*.—Form — Considered crenate. Uniformity — Considered generally uniform.

*Leaf petioles*.—Length — Approximately 7 to 11 mm. Thickness — Approximately 1 to 2 mm. Texture — Glabrous. Color (RHS2001) — Light green, 144B, 144C, N144C, N144D, 145A, 145B and 146D of the Yellow-Green Group.

*Leaf glands*.—Size — Approximately 1-2 mm in height and 1 mm in width. Number — Generally 1-2 per leaf. Type — Reniform. Color (RHS2001) — Brown, 165A, 166A, 166B and 177A of the Greyed-Orange Group, 199A, N199C and N199D of the Grey-Brown Group and 200D of the Brown Group.

*Leaf stipules*.—The stipules are lanceolate in shape and are early deciduous. Ratio of flowering buds to vegetative buds — Generally 2 flower buds per vegetative bud.

Flowers:

*Floral buds*.—General — The floral buds are conic in form, and slightly appressed relative to the bearing shoot. Color (RHS2001) — The mature bud are medium to dark brown (approximately 165A, 166A and 177A of the Greyed-Orange Group, 183A, 183B, 183C, 185A, N186C, 187A and 187B of the Greyed-Purple Group, 199A, N199B and N199C of the Grey-Brown Group and 200A, 200B, 200C and N200A of the Brown Group). The buds are considered hardy in the medium chill zone of Texas. Mature Bud Length — Approximately 8 to 9 mm. Mature Bud Width — Approximately 2 to 4 mm.

*Blooming type*.—Mean date of full bloom in the medium chill zone of Texas was in mid-February (February 18$^{th}$ at Somerville and February 14$^{th}$ at Fairfield experimental plots), a few days before or with the commercial cultivars 'Texking' (patented, U.S. Plant Pat. No. 14,627) and 'Flordaking' (not patented).

*Flower type*.—Showy.

*Flower size*.—Flower diameter at full bloom is approximately 33 to 39 mm.

*Bloom quantity*.—Considered abundant.

*Flower bud frequency*.—Normally 2 per node.

*Petal size*.—Width — Approximately 14 to 15 mm. Length — Approximately 19 to 21 mm.

*Petal form*.—Broadly ovate.

*Petal number*.—Nearly always 5.

*Petal abaxial/adaxial color* (*RHS*2001).—Medium pink when young (62C, 65B, 69A, 69B and 73D of the Red-Purple Group), becoming darker near the petal claw.

*Petal claw*.—Form — The claw is considered truncate in shape. Length — Approximately 1 to 2 mm. Width — Approximately 1 mm.

*Petal margins*.—Generally considered variable, from nearly smooth to slightly undulate.

*Petal apex*.—Generally — The petal apices appear rounded.

*Flower pedicel*.—Length — Average length of 2 mm. Thickness — Approximately 1 mm. Color (RHS2001) — A light green (approximately 144C, 144D, N144A and N144D, 145A and 145B of the Yellow-Green Group).

*Floral nectaries*.—Color (RHS2001) — Variable in color, from medium yellow to medium orange (13A, 13B, 13C of the Yellow Group; 14A, 14B, 14C, 15A, 15B, 15C, 16A and 17C of the Yellow-Orange Group and 24A, 24B, 25B and 25C of the Orange Group).

*Sepals*.—

*Sepal number*.—Generally five per flower. Surface Texture — The surface has a short, fine, wooly texture. Size — Average Height 8.1 mm; Width 4.0 mm. Form — Ovate. Color (RHS2001) Abaxial — Maroon and green with white (approximately 59A, 59B, 60A and 60B of the Red-Purple Group; 144A, 144B and N144C of the Yellow-Green Group; 155A, 155B, 155C, 155D of the White Group; 178A, 178B, 180A and 181A of the Greyed-Red Group and 183A, 183B, 183C, 184A, 184B, 185A, 185B and 187C of the Greyed-Purple Group).

*Floral cup* (*hypanthium*).—Surface Texture — Generally glabrous. Color (RHS2001) — Maroon (approximately 59A, 59B, 60A and 60B of the Red-Purple Group; 178A, 178B, 180A and 181A of the Greyed-Red Group and 183A, 183B, 183C, 184A, 184B, 185A, 185B and 187C of the Greyed-Purple Group).

*Anthers*.—Color (RHS2001) — Dark orange (approximately 28A of the Orange Group and N30A and 34A of the Orange-Red Group).

*Pollen production*.—Pollen is abundant and is a medium to dark yellow color (approximately RHS2001 13A, 13B, 13C, 14A, 14B and 14C of the Yellow Group and 15A, 15B, 15C, 16B and 16C of the Yellow-Orange Group).

*Filaments*.—Size — Variable in length, approximately 9 to 14 mm, with the filaments shorter than the pistil and below the height of the petals. Color — White (approximately 155A, 155B, 155C and 155D of the White Group) and darkening with advanced maturity.

*Pistil*.—General — Taller in height as compared to the general anther height and below the height of the petals. Length — Approximately 16 to 20 mm, including the ovary. Color (RHS2001) — Considered a light yellow-green when young (approximately 1A, 1B, 1C and 1D of the Green-Yellow Group) and becoming slightly darker with advancing senescence.

*Surface texture*.—The variety has a pubescent ovary and style.

Fruit:

*Maturity when described*.—The present variety of fruit is described, as it would be found in its firm ripe condition at full commercial maturity. Under the ecological conditions prevailing in the medium chill zone of Texas it would be ripe in mid-May. The average ripe date at Somerville was May 12$^{th}$ and in Fairfield was May 20$^{th}$.

*Size*.—General — Medium large to large for the season and considered uniform. Average Cheek Diameter — Approximately 60 to 64 mm. Average Suture Diameter — Approximately 58 to 60 mm. Average Axial Diameter — Approximately 52 to 58 mm.

*Fruit form*.—Generally considered round, occasionally exhibiting unequal halves. On occasion the fruit exhibits less symmetry when comparing the suture height with the line opposite the suture. The fruit is generally uniform in symmetry when viewed from the apical aspect.

*Fruit suture*.—Generally, the suture appears as a thin line that extends from the base to the apex, and appears deeper at the apex, forming a shallow basin at the apical point. No apparent callusing or stitching exists along the suture line. Fruit suture depth at the midpoint is less than 1 mm. Color (RHS2001) — Maroon, 46A and 53A of the Red Group, 59A, 59B and 60A of the Red-Purple Group and 183A, 183B, 185A, N186C, 187B and 187C of the Greyed-Purple Group.

*Ventral surface*.—Form — Considered uniform.

*Stem cavity*.—Width — Approximately 14 to 17 mm. Length — Approximately 21 to 29 mm. Depth — Approximately 9 to 10 mm.

*Fruit base*.—Round and flat.

*Fruit apex*.—Flat and round.

*Fruit stem*.—Length — 6 to 10 mm. Thickness — Approximately 3 mm. Color (RHS2001) — Light green, varies from 139D of the Green Group to N144D, N144B, 145A and 145B of the Yellow-Green Group.

*Fruit skin*.—Generally considered medium or average in thickness. Surface Texture — Light, medium pubescence. Skin Acidity — Considered neutral. Tenacious to Flesh — Yes at commercial maturity. Tendency to Crack — No cracking observed. Skin Color (RHS2001) — Generally — Variable, with approximately 60-80% of the fruit surface covered with a medium red to maroon blush. The fruit skin over color pattern varies from marbled to solid. Blush Color (RHS2001) — Medium red to maroon, 46A and 53A of the Red Group, 59A, 59B and 60A of the Red-Purple Group and 183A, 183B, 185A, N186C, 187B and 187C of the Greyed-Purple Group. Skin Ground Color (RHS2001) — Light to medium yellow, 1C and 1D of the Green-Yellow Group, 2C, 2D and 3D of the Yellow Group and 160B and 160C of the Greyed-Yellow Group.

*Flesh color* (*RHS*2001).—White with some dark pink fibers, 155B and 155D of the White Group and 58A, 59C, 60B, 60C and 61B of the Red-Purple Group. Anthocyanin intensity in the flesh is generally medium to strong next to the skin, weak to medium centrally and weak next to the stone.

*Flesh fibers*.—Present throughout the flesh.

*Stone cavity color* (*RHS*2001).—White, 155B and 155D of the White Group.

*Flesh texture*.—Generally, the flesh is considered firm at commercial maturity.

*Ripening*.—Generally the fruit of the present variety ripens evenly.

*Flavor*.—Considered sweet (average Brix 12.9) and a rich, subacid flavor.

Stone:

*Attachment*.—Clingstone at commercial maturity.

*Stone size*.—Length — Approximately 30 to 33 mm. Width — Approximately 20 to 22 mm. Thickness — Approximately 16 mm.

*Fibers*.—Generally a few fibers are attached along the entire surface of the stone.

*Stone form*.—Varies between elliptical and obovate.

*Stone base*.—The stone is narrow.

*Hilum*.—The hilum is less than 1 mm wide.

*Stone apex angle*.—Medium to wide.

*Stone shape*.—Considered variable. Normally, ovoid to elongated.

*Stone surface*.—Surface Texture — Consists of a combination of single, rosettes and chains of pits. Ridges — Numerous fine ridges are present basally and converge towards the base of the stone.

*Ventral edge*.—Medium.

*Dorsal edge*.—Shape — Grooved and having moderately rough edges.

*Stone color* (*RHS*2001).—The color of the dry stone is light brown, 164B, 164C, 165C and 165D of the Greyed-Orange Group. The color of the inside surface of the endocarp is primarily light brown, 158A of the Yellow-White Group, 159A and 159B of the Orange-White Group and 164C and 165D of the Greyed-Orange Group.

*Tendency to split*.—Splitting is uncommon.

*Kernel*.—The kernel fills the endocarp at harvest and measures approximately 4 mm in thickness, 10 mm in width, and 15-17 mm in length. The colors (RHS2001) of the fresh kernels are ivory, 155B and 155D of the White Group and 158A, 158B and 158C of the Yellow-White Group. When dried the shriveled kernels measure approximately 2 mm in thickness, 9 mm in width and 13-15 mm in length. The colors of the dried kernels are tan to light brown, 158A of the Yellow-White Group, 161C, 161D and 162D of the Greyed-Yellow Group and 163D, 164C, 164D, 165B and 165C of the Greyed-Orange Group.

*Use*.—The subject variety, 'TX2B449LW', is considered to be a peach tree of early-season maturity, which produces subacid, white-fleshed fruit which are very firm, and have a 60-80% red to maroon blush over a yellow ground color, and which are useful for fresh fruit market.

*Keeping quality*.—Average. Retains firmness and flavor after 14 days of refrigeration at 3-5° C.

*Resistance to insects and disease*.—No atypical resistances/susceptibilities were noted under normal cultural practices to date.

*Shipping quality*.—Average. Fruit does not develop internal breakdown and retains good firmness and eating quality after 14 days of refrigeration at 3-5° C.

Although the new variety of peach tree possesses the described characteristics when grown under the ecological conditions prevailing in the medium chill zone of Texas in Somerville and Fairfield, it will be understood that variations of the usual magnitude and characteristics incident to the changes in growing conditions, fertilization, pruning, and pest control are to be expected.

What is claimed is:

1. A new and distinct variety of peach tree named 'TX2B449LW', as illustrated and described herein.

* * * * *